United States Patent [19]

Tanabe et al.

[11] Patent Number: 4,966,961

[45] Date of Patent: Oct. 30, 1990

[54] POLYMALEIMIDE FROM POLYARYLENE POLYAMINE AND PROCESS FOR THE PREPARATION THEREOF

[75] Inventors: Yoshimitsu Tanabe; Keizaburo Yamaguchi; Tatsuhiro Urakami; Akihiro Yamaguchi, all of Kanagawa, Japan

[73] Assignee: Mitsui Toatsu Chemicals, Inc., Tokyo, Japan

[21] Appl. No.: 351,705

[22] Filed: May 15, 1989

[30] Foreign Application Priority Data

May 19, 1988 [JP]  Japan ................... 63-122645

[51] Int. Cl.$^5$ ............................. C08G 73/12
[52] U.S. Cl. ....................... 528/345; 525/540;
   528/312; 528/313; 528/315; 528/318; 528/319
[58] Field of Search ............... 528/345, 312, 313, 315, 528/318, 319; 525/540

[56]  References Cited

U.S. PATENT DOCUMENTS 3,868,351  2/1975  Hand et al. ................... 528/345
4,539,392  9/1985  Kadoi et al. ................... 528/345

Primary Examiner—Harold D. Anderson

Attorney, Agent, or Firm—Burns, Doane, Swecker & Mathis

[57] ABSTRACT

The present invention relates to polymaleimide compounds having the following chemical structure:

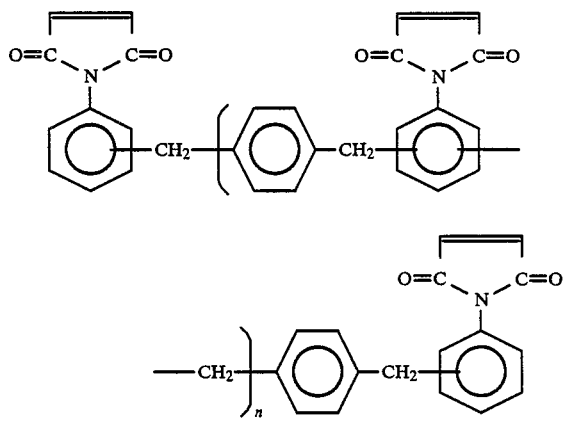

wherein n represents an integer of from 0 to about 50 and to a process for preparing the same.

17 Claims, 2 Drawing Sheets

POLYMALEIMIDE FROM POLYARYLENE POLYAMINE AND PROCESS FOR THE PREPARATION THEREOF

BACKGROUND OF THE INVENTION (a) Field of the Invention

This invention relates to polymaleimide compounds useful as raw materials for addition-type polyimides and also to a process for preparing the polymaleimide compounds. More specifically, the process comprises reacting specific aromatic amine resins with maleic anhydride.

(b) Description of the Prior Art

Polymaleimides obtained from conventional bismaleimides such as N,N'-(4,4'-methylenediphenylene)-bismaleimide are known to exhibit excellent heat resistance. These polyimides are produced by polymerizing bismaleimide or by copolymerizing bismaleimide compounds with amines. These polyimides are used widely for impregnating varnishes, laminates, and molded and otherwise formed articles.

Conventional bismaleimide compounds generally have high melting points. Therefore, it has been necessary to use them in the form of solutions. Moreover, conventional bismaleimide compounds have poor solubility in general-purpose organic solvents, and thus special solvents having a high boiling point and hygroscopicity such as N-methylpyrrolidone or N,N-dimethylacetamide must be employed. Impregnating varnishes prepared by dissolving bismaleimide compounds in such solvents are expensive due to the high price of the solvent. In addition, the solvent tends to remain in prepregs formed from the varnishes, which is a major cause of considerable reduction in the performance of the resulting laminates.

Thus, it is desirable to provide maleimide compounds having solubility in general-purpose organic solvents, as well as heat resistance in the fields of matrix resins for heat-resistant composite materials and heat-resistant molding materials. It is also desirable to develop maleimide compounds useful as raw materials for producing thermosetting resins that retain excellent dimensional stability in a manner similar to electrical-insulating molded articles of thermosetting resins derived from conventional bismaleimide compounds which exhibit superior impact resistance, flexibility and toughness.

SUMMARY OF THE INVENTION

The present invention overcomes the problems and disadvantages of the prior art by providing polymaleimide compounds that exhibit superior properties than prior art maleimide compounds.

It is an object of this invention to provide polymaleimide compounds having high solubilities in organic solvents, excellent heat resistance and superb molding processability.

Another object of this invention is to provide a polymaleimide compound that has application as a thermosetting resin, which upon copolymerization with an amine and post-curing, gives a hardened product having high flexural strength and excellent impact resistance, flexibility and toughness.

A further object of this invention is to provide a process for preparing the polymaleimide compounds.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein, the invention provides a polymaleimide compound represented by the formula (I):

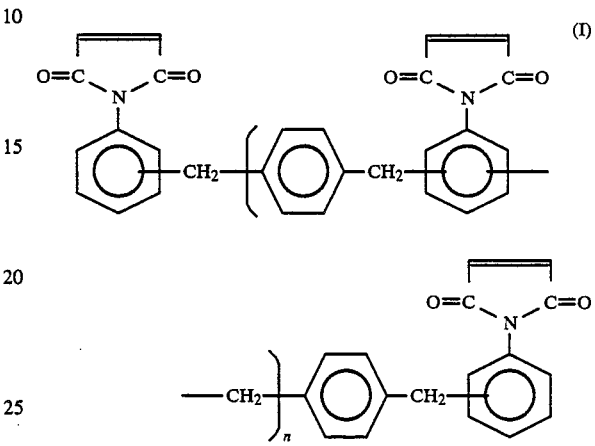

wherein n represents an integer of from 0 to 50.

The invention also provides a process for preparing a polymaleimide compound represented by the formula (I), comprising reacting maleic anhydride and an aromatic amine compound represented by the formula (II):

(II)

NH₂ ... NH₂ ... NH₂

[structure showing aromatic amine with CH₂ linkages]

wherein n has the same meaning as defined above.

The accompanying drawings, which are incorporated in and constitute a part of this specification, illustrate several exemplary embodiments of the invention and together with the description, serve to explain the principles of the invention.

DETAILED DESCRIPTION OF THE INVENTION

Figure 1:
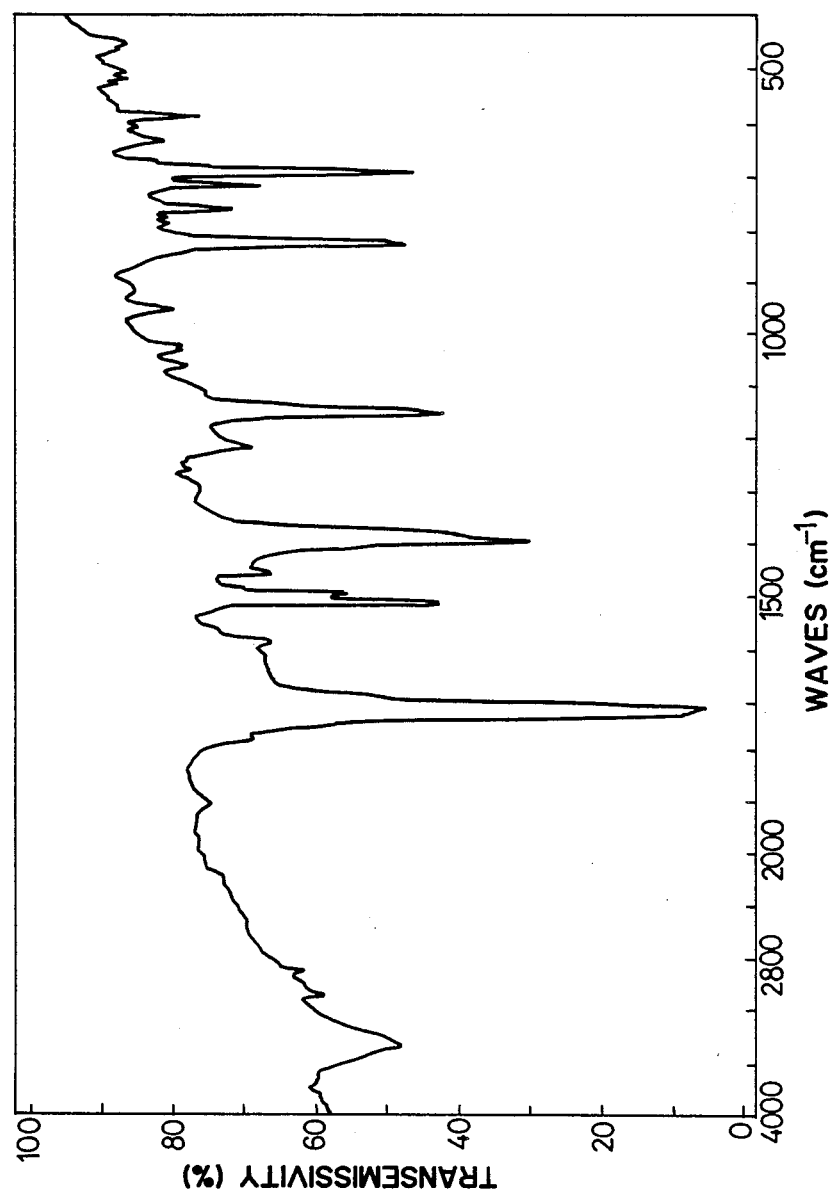
FIG. 1 is a diagram showing the results of an IR analysis of the polymaleimide compound obtained in Example 1.

Reference will no be made in detail to the present preferred embodiments of the invention.

As an example of the melting points and heat resistances of polymaleimide compounds of the invention, the 5% weight loss temperatures of several polymaleimide compounds of this invention will be compared to the weight loss temperature of conventional N,N'-(4,4'-methylenediphenylene)bismaleimide and are set forth in Table 3. Conventional bismaleimide compounds generally have high melting points, generally 150° C. or higher. N,N'-(4,4'-methylenediphenylene)-bismaleimide was found to have a melting point of from about 156° C. to about 158° C. In contrast, the melting points of polymaleimide compounds according to this invention are lower, generally from about 50° C. to about 200° C., particularly from about 80° C. to about 160° C., preferably from about 80° C. to about 130° C. Polymaleimide compounds have such low melting points that they can be polymerized in a molten state without a solvent. It is hence possible to use prepolymer melts directly as impregnating varnishes to produce laminates. Even when molded articles are produced by compression molding, transfer molding or a similar method, these polymaleimide compounds are absolutely free of the problem of remaining solvent and thus their application field can be broadened to attain efficient work and save energy.

The 5% weight loss temperatures in air of the polymaleimide compounds of the invention are all as high as at least 400° C. Thus, their heat resistance properties are fully satisfactory.

As set forth in Table 4 the solubilities of the polymaleimide compounds of the invention in 1,2-dichloroethane, acetone and methyl ethyl ketone range from 35 wt.% to 50 wt.% at 25° C. and are considerably higher compared to those of the conventional bismaleimides, particularly N,N'-(4,4'-methylenediphenylene)-bismaleimide. It is a characteristic feature of the polymaleimide compounds of this invention that a solvent having a high boiling point and hygroscopicity such as N,N-dimethylacetamide or N,N-dimethylformamide which has been indispensable in conventional maleimide compounds, can be replaced by a volatile solvent having a low boiling point. It is hence possible to reduce the problem of the remaining solvent which causes reduction of the performance of laminates or molded articles. Such a solvent is also preferred for improving work efficiency and attaining energy saving. The polymaleimide compounds of this invention have numerous applications in various fields of industry such as electrical insulating materials, heat-resistant adhesives, and paints.

Polyimides obtained from the polymaleimide compounds of this invention have excellent heat resistance as demonstrated in Table 5, namely, due to their high flexural strength and high moduli of flexural elasticity, heat distortion temperatures of at least 290° C. and thermal decomposition initiation temperatures of at least 340° C.

The present process for preparing the polymaleimide compounds of the invention is set forth below.

The present inventors developed a process for preparing an aromatic amine compound employed in the present invention. The process is described in Japanese Patent Application Nos. 252517/1987 and 282048/1987.

The aromatic amine compound employed as a raw material is a compound represented by the formula (II). This compound can be produced industrially with ease by reacting aniline with (a) a bishalogenomethyl derivative represented by the following formula (III):

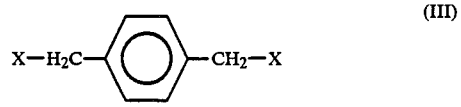

wherein X represents a halogen atom or with (b) an aralkyl alcohol derivative represented by the following formula (IV):

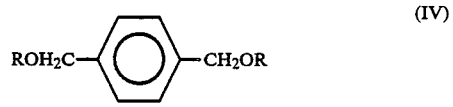

wherein R is selected from the group consisting of a hydrogen atom, an acyl group and a lower alkyl group having not more than 4 carbon atoms.

Exemplary suitable bishalogenomethyl derivatives useful in preparing the aromatic amine compound include α,α'-dichloro-p-xylene, α,α'-diacetoxy-p-xylene, α,α'-dipropionoxy-p-xylene, α,α'-di-n-butyloxy-p-xylene, α,α'-dimethoxy-p-xylene, α,α'-diethoxy-p-xylene, α,α'-diisopropoxy-p-xylene, α,α'-di-n-propoxy-p-xylene, α,α'-di-n-butoxy-p-xylene, α,α'-di-sec-butyoxy-p-xylene, and α,α'-diisobutoxy-p-xylene.

The aromatic amine compound can be prepared by a condensation reaction of a bishalogenomethyl derivative of the formula (III) or the aralkyl alcohol derivative of the formula (IV) with aniline in a molar ratio of bishalogenomethyl derivative or aralkyl alcohol derivative to aniline of about 1 to 1–15 at from about 170° to about 240° C. for from about 10 to about 40 hours in the presence of an acid catalyst such as hydrochloric acid.

After completion of the reaction, the reaction mixture is preferably neutralized with an alkali such as caustic soda and then washed with water. In some instances, it is preferable to drive out excess aniline under reduced pressure.

The aromatic amine resin represented by the formula (II) and maleic anhydride are reacted in an organic solvent to form a polymaleamic acid represented by the following formula (V):

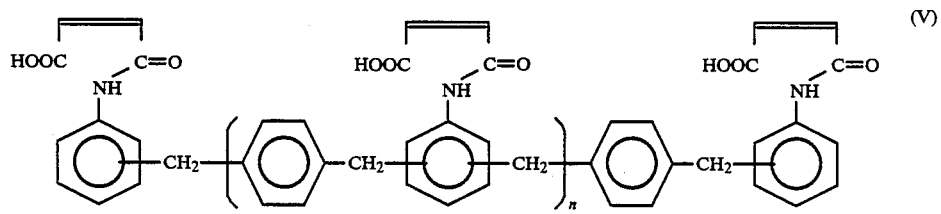

wherein n represents an integer of from 0 to 50. Maleic anhydride may be employed in an amount of from about 0.8 to about 2.0 equivalents, preferably from about 1 to about 1.5 equivalents per equivalent of amino groups in the aromatic amine resin. Exemplary suitable reaction solvents for use in the above reaction include halogenated hydrocarbons such as chloroform, methylene chloride, dichloroethane and trichloroethylene; ketones such as acetone, methyl ethyl ketone, cyclohexanone and diisopropyl ketone; ethers such as diethyl ether, tetrahydrofuran, dioxane and 2-methoxyethanol; aromatic compounds such as benzene, toluene and chlorobenzene; aprotic polar solvents such as acetonitrile, N,N-dimethylformamide, N,N-dimethylacetamide, dimethylsulfoxide, N-methylpyrrolidone and 1,3-dimethyl-2-imidazolidinone. Although no particular limitation is imposed on the amount of the solvent to be used, it is generally sufficient to employ a solvent in an amount of from about 1 to about 10 times by weight of the sum of the raw materials.

The polymaleamic acid is then cyclized and dehydrated to form a polymaleimide compound represented by the formula (I). This cyclization and dehydration reaction can be conducted by any known process in which acetic anhydride is used as a dehydrating agent and the reaction is carried out in the presence of a base and a catalyst in an organic solvent (Japanese Patent Publications 23250/1971, 40231/1974 and 52660/1984). No particular limitation is imposed on the upper limit of the amount of acetic anhydride to be used in the cyclization and dehydration reaction. However, it is generally used in an amount of from about 1 to about 4 times equivalents per equivalent of the amino groups in the aromatic amine compound.

Exemplary suitable catalysts include alkaline earth metal oxides, iron(II,III), nickel(II), manganese(II,III), copper(I,II) and cobalt(II,III) carbonates, sulfates, phosphates and acetates. Preferably, nickel(II) acetate, cobalt(II) acetate and/or magnesium oxide are employed. Although these catalysts exhibit sufficient effects when used singly, they may also be used in combination. The catalyst is preferably used in an amount of from about $5 \times 10^{-4}$ to about 0.1 mole per mole of the amino groups in the aromatic amine compound.

Exemplary suitable bases useful in the practice of the above process include alkali metal acetates and tertiary amines. Preferably sodium acetate, potassium acetate, trimethylamine, triethylamine, tributylamine and the like are employed. The base may be used in an amount of from about 0.05 to about 1.1 equivalents per equivalent of amino groups in the aromatic amine compound.

No other particular limitations are imposed on the process of this invention. It is not essential for the preparation of the polymaleimide compound to isolate the polymaleamic acid formed as an intermediate in the first step. The cyclization and dehydration reaction can be carried out in the same solvent. The reaction temperature ranges from about 20° C. to about 150° C., preferably from about 20° C. to about 80° C., and the reaction time ranges from about 0.5 hour to about 9 hours. Upon pouring the reaction mixture into water or methanol after completion of the reaction, the intended product can be obtained in the form of crystals.

The weight average molecular weight of the polymaleimide compound ranges from about 400 to about 15,000, and has a melting point of from about 50° C. to about 200° C. Depending on the number of n in the formula (1), the polymaleimide compound of this invention has a distribution of n, which can be chosen as desired. For example, as will also become apparent from examples subsequently described, the polymaleimide compound may be a mixture of from about 5% to about 100%, preferably from about 5% to about 85% of the polymaleimide compound having the formula (I) where n is 0 (n=0) and from about 80% to about 1% of at least one polymaleimide compound having the formula (I) wherein n is at least 3 (n≧3). The percentages can be measured by high performance liquid chromatography.

The polymaleimide compounds of this invention are organic-solvent-soluble polymaleimides having melting points lower than conventional bismaleimides such as N,N'-(4,4'-methylenediphenylene)bismaleimide. Further, the solubilities of the polymaleimide compounds in general-purpose organic solvents are very high. The low-melting-point and solvent-soluble polymaleimide compounds can be polymerized in a molten state. When a solvent is employed, a general-purpose organic solvent may be used. The polymaleimide compounds of the invention overcome the problem of remaining solvent, causes deterioration of laminates and/or molded articles, and improves flexibility and results in much efficient work.

The invention will be further clarified by the following examples, which are intended to be purely exemplary of the invention.

SYNTHESIS EXAMPLE 1

111.6 g (1.2 moles) of aniline and 70.0 g (0.4 moles) of $\alpha,\alpha'$-dichloro-p-xylene were charged in a reactor equipped with a stirrer and a thermometer. While feeding nitrogen gas through the reactor, the contents were heated. Although exothermic heat was recognized from the internal temperature of about 30° C., the contents were heated and maintained at 85°-100° C. for 3 hours (first step reaction). Further heating was conducted at 190°-200° C. for 20 hours (second step reaction). The reactor was then cooled to lower its internal temperature to 95° C., followed by addition of 230 g of a 15% aqueous solution of caustic soda. The resultant mixture wa stirred and neutralized. After allowing the thus-prepared mixture to stand, the lower layer, namely, the water layer was separated and removed. Then, 300 g of saturated saline were added to the remaining organic layer to wash it, followed by separation and removal of a water layer. The resulting organic solution was heated and dehydrated under a nitrogen gas stream and then filtered under pressure to remove inorganic salts and the like. The organic solution thus obtained was concentrated in a vacuum of 2-3 mmHg, thereby recovering 48.5 g of unreacted aniline. The residue was removed and 100 g of an aromatic amine compound having a pale yellowish brown color were produced.

The aromatic amine compound was analyzed by high-performance liquid chromatography (GPC column method). The aromatic amine compound of the formula (II) was found to have the following composition:

|  | Area % |
| --- | --- |
| n = 0 | 27.8 |
| n = 1 | 19.2 |
| n = 2 | 14.0 |
| n = 3 | 11.8 |
| n ≧ 4 | 27.2 |

The GPC column method was conducted under the following conditions:
Columns: "Shodex GPC-A-802" (trade name) x 2
Mobile phase: Tetrahydrofuran (flow rate: 1 ml/min)
Detector: RI (REFRACTIVE INDEX) DETECTOR manufactured by Japan Analytical Industry Co., Ltd.

The amine equivalent of the compound as measured by the perchloric acid-glacial acetic acid method was 0.65 equivalent per 100 g of the compound, while its softening point as measured by a ring and ball softening point measuring apparatus in accordance with JIS-K-2548 was 64° C. Its average molecular weight was 880.

SYNTHESIS EXAMPLE 2

111.6 g (1.2 moles) of aniline, 66.5 g (0.4 mole) of α,α'-dimethoxy-p-xylene and as a catalyst, 62.6 g (0.6 mole) of a 35% aqueous solution of hydrochloric acid were charged in a reactor equipped with a stirrer, a thermometer and a Dean-Stark azeotropic distillation trap. The contents were heated while feeding nitrogen gas through the reactor. From the internal temperature of about 110° C., water distilled to the trap was removed from the system. When heated further, distillation of methanol was observed from about 130° C. While distilling out the resulting methanol, heating of the contents was continued. After the temperature reached 170° C., the contents were maintained at the same temperature for 3 hours. Evolution of methanol ceased substantially, and the contents were thereafter continuously heated to react at 190°-200° C. for 12 hours. The reactor was then cooled to lower the internal temperature to 95° C., followed by addition of 168 g of a 15% aqueous solution of caustic soda. The resultant mixture was stirred and neutralized. After allowing the thus-prepared mixture to stand, the lower layer, namely, the water layer was separated and removed. Then, 300 g of saturated saline were added to the remaining organic layer to wash it, followed by the separation and removal of a water layer. The resulting organic solution was heated and dehydrated under a nitrogen gas stream and then filtered under pressure to remov inorganic salts and the like. The organic solution thus obtained was concentrated in a vacuum of 2-3 mmHg, thereby recovering 51.9 g of unreacted aniline. The residue was taken out to obtain 94.5 g of an aromatic amine compound having a pale yellowish brown color.

The composition of the aromatic amine compound obtained as described above was analyzed by high-performance liquid chromatography. As a result, the aromatic amine compound of the formula (II) was found to have the following composition:

|       | Area % |
| ----- | ------ |
| n = 0 | 28     |
| n = 1 | 16.8   |
| n = 2 | 10.5   |
| n = 3 | 7.8    |
| n ≧ 4 | 36.9   |

The amine equivalent of the compound as measured by the perchloric acid-glacial acetic acid method was 0.578 equivalent per 100 g of the resin, while its softening point as measured by a ring and ball softening point measuring apparatus in accordance with JIS-K-2548 was 68° C. Its average molecular weight was 960.

SYNTHESIS EXAMPLES 3-5

Aromatic amine compounds represented by the formula (II) were prepared in similar manners as in Synthesis Examples 1 and 2 except that the amount of aniline, the amount and kind of the bishalogenomethyl derivative and aralkyl alcohol represented by the formulae (III) and (IV) respectively, the kind and amount of the catalyst, and the reaction conditions set forth Table 1 were employed.

TABLE 1

| Synthesis Example | Amount of aniline (moles) | Bishalogenomethyl or aralkyl alcohol derivative Kind | Amount (mole) | Catalyst Kind | Amount (mole) | Reaction conditions Temp./Time (°C.) (hrs) | Aromatic amine compound Composition (LC, %) n = 0 | n = 1 | n = 2 | n ≧ 3 | Yield (g) | Softening point, °C. | Amine value (eq/100 g) |
| --- | --- | --- | --- | --- | --- | --- | --- | --- | --- | --- | --- | --- | --- |
| 3 | 4.0 | α,α'-Dichloro-p-xylene | 0.4 | HCl | 1.8 | 190-200/23 | 73 | 19 | 6.6 | 1.4 | 98.5 | Oily | 0.64 |
| 4 | 0.6 | α,α'-Dimethoxy-p-xylene | 0.4 | HCl | 0.3 | 110-170/5 200-205/15 | 10 | 7.4 | 6.0 | 76.6 | 98 | 120 | 0.53 |
| 5 | 1.2 | α,α'-Dihydroxy-p-xylene | 0.4 | HCl | 0.6 | 130-170/5 200-120/16 | 28 | 19 | 14 | 39 | 100 | 66 | 0.60 |

EXAMPLE 1

In a reaction flask fitted with a stirrer and a thermometer, 35.8 g (0.358 mole) of maleic anhydride and 40 g of acetone were charged and the maleic anhydride was dissolved in the acetone. Upon dropwise addition of a solution formed by dissolving 50 g of the aromatic amine compound (amine equivalent: 0.65 eq/100 g) obtained in Synthesis Example 1 in 50 g of acetone, crystals were formed. The resulting mixture was stirred at 25° C. for 3 hours. Thereafter, 8.5 g of triethylamine were added, followed by stirring at 25° C. for 30 minutes. Subsequent to the addition of 0.35 g of magnesium-(III) oxide and 0.035 g of cobalt acetate tetrahydrate, 45.5 g of acetic anhydride were charged. The thus-prepared mixture was stirred at 50°-55° C. for 3 hours. After cooling the reaction mixture to 25° C., it was added dropwise under stirring to 1 l of water. Crystals thus formed were collected by filtration, washed with water and then dried, thereby obtaining a polymaleimide compound as brown crystals.

The composition of the polymaleimide compound obtained as described above was analyzed by high-performance liquid chromatography. As a result, the polymaleimide compound of the formula (I) was found to have the following composition:

|       | Area % |
| ----- | ------ |
| n = 0 | 25     |
| n = 1 | 23     |
| n = 2 | 17     |
| n ≧ 3 | 35     |

Its yield and melting point were 74.2 g (98.1%) and 115°-130° C., respectively. Further, the results of an IR analysis of the compound are diagrammatically shown in FIG. 1. IR (KBr, cm-⁻¹) 1770 and 1710 (imido bonds)

EXAMPLE 2

In a reaction flask fitted with a stirrer and a thermometer, 35.2 g (0.352 mole) of maleic anhydride and 35 g of acetone were charged and the maleic anhydride was dissolved in the acetone. A solution which was formed by dissolving 50 g of the aromatic amine compound (amine equivalent: 0.64 eq/100 g) obtained in Synthesis Example 3 was added dropwise into g of acetone, and the resultant mixture was stirred at 25° C. for 3 hours. Crystals thus formed were collected by filtration, washed and then dried, thereby obtaining a polymaleamic acid as yellow crystals.

Its yield and melting point were 57 g (70%) and 160°–210° C., respectively.

Figure 2:
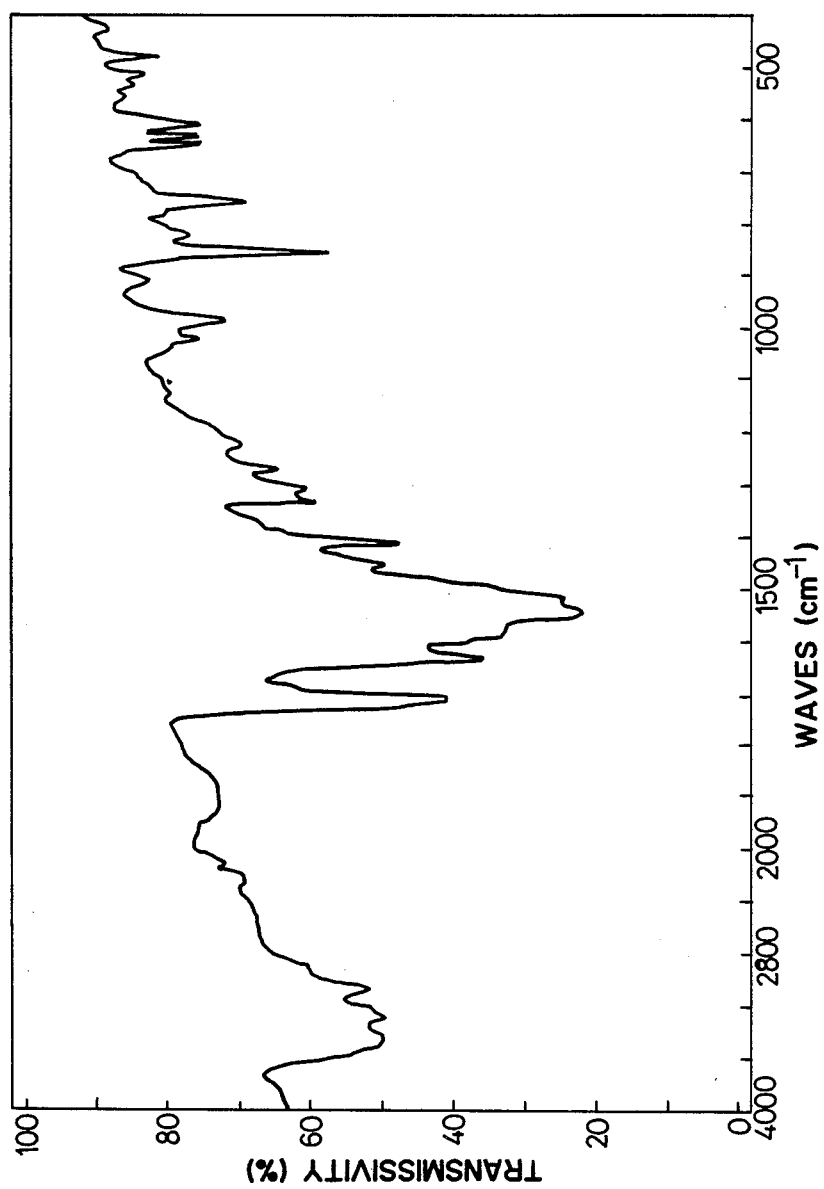
FIG. 2 is a diagram illustrating the results of an IR analysis of a polymaleamic acid obtained in Example 2.

Further, the results of an IR analysis of the polymaleamic acid are diagrammatically shown in FIG. 2.

Fifty-seven grams of the polymaleamic acid thus obtained were suspended in 120 g of acetone, followed by the addition of 6.1 g of triethylamine. The resultant mixture was stirred at room temperature for 30 minutes. Thereafter, 0.25 g of magnesium(II) oxide and 0.025 g of cobalt oxide tetrahydrate were added and 30 g of acetic anhydride were charged. The thus-prepared mixture was stirred at 50°–55° C. for 3 hours. After cooling, the reaction mixture was added dropwise under stirring into 1 l of water. Crystals thus formed were collected by filtration, washed and then dried, thereby obtaining a polymaleimide compound as brown crystals.

The composition of the polymaleimide compound obtained as described above was analyzed by high-performance liquid chromatography. As a result, the polymaleimide compound of the formula (I) was found to have the following composition:

|  | Area % |
|---|---|
| n = 0 | 77.8 |
| n = 1 | 17.1 |
| n = 2 | 2.6 |
| n ≧ 3 | 2.5 |

Yield: 51 g (97%)
Melting point: 80°–140° C.
IR (KBr, cm⁻¹): 1770 and 1710 (imido bonds)

EXAMPLES 3–5

In a similar manner to Examples 1 and 2, the aromatic amine compound obtained in the above synthesis examples were separately reacted with maleic anhydride to obtain polymaleimide compounds represented by the formula (I).

The kinds and amounts of the aromatic amine compounds used, the amounts of maleic anhydride employed, and the yields and compositions of the thus-obtained polymaleimide compounds are given in Table 2.

The melting points and 5% weight loss temperatures of the polymaleimide compounds obtained in Examples 1, 3 and 4 and those of a known bismaleimide compound are shown in Table 3, while their solubilities in various solvents are given in Table 4.

TABLE 2

| Example | Aromatic amine compound Kind and amount | Amine value (eq. 100 g) | Amount of maleic acid anhydride (g) | Polymaleimide compound Yield (g) | Yield (%) | Composition by LC (%) | | M.P. (° C.) |
|---|---|---|---|---|---|---|---|---|
| 3 | Synthesis Example 3 (50 g) | 0.64 | 35.2 | 74 | 98 | n = 0<br>n = 1<br>n = 2<br>n ≧ 3 | 73.3<br>18.1<br>5.7<br>2.9 | 76–116 |
| 4 | Synthesis Example 4 (50 g) | 0.53 | 32.5 | 69.3 | 98 | n = 0<br>n = 1<br>n = 2<br>n ≧ 3 | 10.0<br>7.4<br>6.0<br>76.6 | 130–160 |
| 5 | Synthesis Example 5 (50 g) | 0.60 | 33.0 | 72 | 97 | n = 0<br>n = 1<br>n = 2<br>n ≧ 3 | 26.0<br>23.0<br>16.0<br>35.0 | 116–137 |

TABLE 3

|  | Polymaleimide compound | M.P. (°C.) | 5% Weight loss temp. |
|---|---|---|---|
| Example 1 | 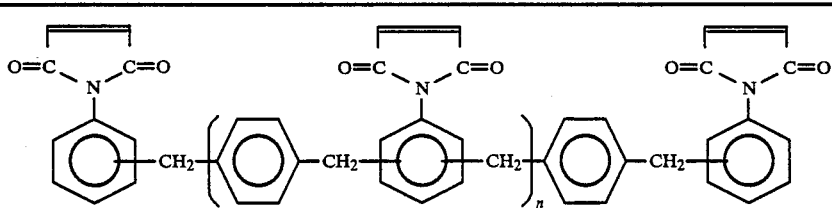 | 115–130 | 487° C. |
| Example 3 | " | 76–116 | 468° C. |
| Example 4 | " | 130–160 | 496° C. |
| Comparative Example | N,N'-(4,4'-Methylenediphenylene)bismaleimide | 156–158 | 506° C. |

TABLE 4

| | Solubility of polymalemide compound (25° C., wt. %) | | | |
|---|---|---|---|---|
| Solvent | Example 1 | Example 3 | Example 4 | N,N'-(4,4'-methylene-phenylene)bismaleimide |
| Acetone | >50 | >50 | >30 | 5 |
| Methyl ethyl ketone | >40 | >40 | >20 | 3 |
| Chloroform | >20 | >20 | >10 | 7 |
| 1,2-Dichloroethane | >35 | >35 | >25 | 7 |
| 1,4-Dioxane | >50 | >50 | >50 | 9 |
| Tetrahydrofuran | >50 | >50 | >50 | 6 |
| Anisole | 5 | 5 | 2 | <1 |
| Toluene | 2 | 2 | — | <1 |
| N,N-Dimethylacetamide | >50 | >50 | >50 | 23 |

APPLICATION EXAMPLES

The polymaleimide compound obtained in each of the foregoing examples and 4,4'-diaminodiphenylmethane were charged at the corresponding make-up weight ratio given in Table 5 into a stainless steel vessel equipped with a stirrer, a reflux condenser and a nitrogen gas inlet tube. The compounds were heated, molten and reacted at 180° C. for 20 minutes. After defoaming the reaction mixture at 150° C. under reduced pressure (10–15 mmHg) for 30 minutes, the reaction mixture was cooled to room temperature to obtain a resin composition in a form solidified like transparent brown glass.

While heating the composition into a melt, it was filled in molds that had been heated to 180° C. The composition wa maintained at 50 kg/cm² and 200° C. for 30 minutes, thereby compression-molding the same. The resulting moldings were removed from the molds, followed by post curing for 4 hours in an oven of 250° C. to obtain as test pieces hardened products of 127 mm long, 12.7 mm wide and 6.4 mm thick.

The heat distortion temperature of one of the test pieces was measured in accordance with ASTM-D-648, while another one of the test pieces was subjected to a bending test in accordance with ASTM-D-790. In addition, the thermal decomposition initiation temperature of one of the test pieces was also conducted at a heating rate of 10° C./min in air. The results are shown in Table 5 — Application Examples.

Other embodiments of the invention will be apparent to those skilled in the art from consideration of the specification and practice of the invention disclosed herein. It is intended that the specification and examples be considered as exemplary only, with a true scope and spirit of the invention being by the following claims.

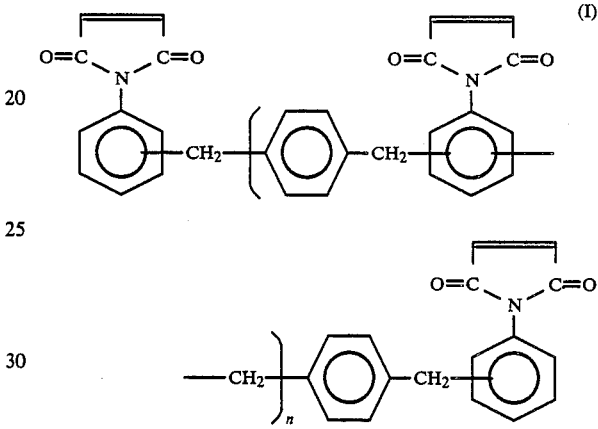

wherein n represents an integer of from 0 to 50.

2. The polymaleimide of claim 1 wherein said polymaleimide has a weight average molecular weight of from about 400 to about 15,000 and a melting point of from about 50° C. to about 200° C.

3. The polymaleimide of claim 2 wherein the melting point is from about 70° C. to about 160° C.

4. A process for preparing a polymaleimide comprising reacting an aromatic amine compound of the formula (II):

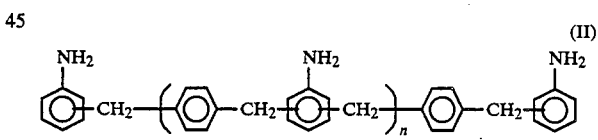

wherein n represents an integer of from 0 to about 50, with maleic anhydride to form a polymaleimide of the formula (I):

TABLE 5

| | | Application Examples | | | |
|---|---|---|---|---|---|
| Application Example | Polymaleimide compound (wt. parts) | Amine used (wt. parts) | Flexural strength (kg/cm²) | Modulus of flexural elasticity (kg/cm²) | Heat distortion temp. (°C.) | Thermal Decomposition temp. (°C.) |
| 1 | Example 1 (50) | 4,4'-Diamino-diphenylmethane (100) | 12.8 | 351 | >290 | 341 |
| 2 | Example 4 (50) | 4,4'-Diamino-diphenylmethane (100) | 13.0 | 360 | >290 | 350 |
| Comparative Example | KELIMIDE 1050* ™ | | 8.6 | 352 | 285 | 333 |

*NIPPON POLYIMIDE CO.: Addition type polyimide consisting of N,N-(4,4'-methylenephenylene) bismaleimide and 4,4'-diaminodiphenylmethane

We claim:

1. A polymaleimide represented by the following formula (I):

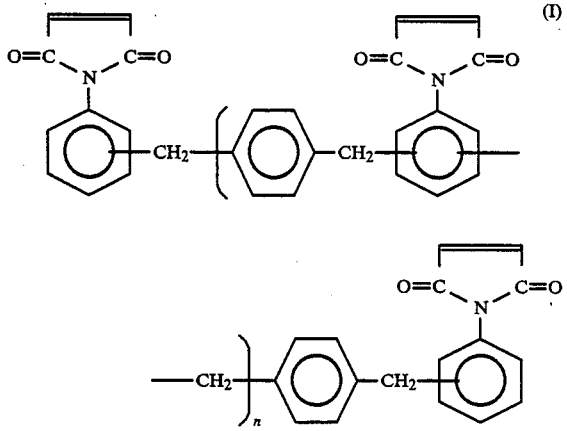

(I)

wherein n represents an integer of from 0 to about 50.

5. The process of claim 4 wherein said aromatic amine compound and said maleic anhydride are reacted in from about 1 to about 10 parts by weight of an organic solvent per part by weight of the sum of said aromatic amine compound and maleic anhydride to form a polymaleamic acid; and then said polymaleamic acid is cyclized and dehydrated in the presence of acetic anhydride, a base and a catalyst.

6. The process of claim 5 wherein maleic anhydride is present in an amount of from 1 to about 1.5 equivalents per equivalent of amino groups present in said aromatic amine compound.

7. The process of claim 5 wherein acetic anhydride is present in an amount of from about 1 to about 4 equivalents per equivalent of amino groups in said aromatic amine compound.

8. The process of claim 5 wherein said catalyst is selected from the group consisting of the oxides of alkaline earth metals and the carbonates, sulfates, phosphates and acetates of iron(II,III), nickel(II), manganese(II,III), copper(I,II) and cobalt(II,III).

9. The process of claim 5 wherein said base is selected from the group consisting of an alkali metal acetate and a tertiary amine.

10. The process of claim 5 wherein said base is selected from the group consisting of sodium acetate, potassium acetate, trimethylamine, triethylamine, and tributylamine.

11. The process of claim 9 wherein said base is present in an amount of from about 0.05 to about 1.1 equivalents per equivalent of amino groups in said aromatic amine compound.

12. The process of claim 5 wherein said polymaleamic acid is cyclized and dehydrated at a temperature of from about 20° C. to about 150° C.

13. The process of claim 4 wherein said aromatic amine compound is prepared by reacting aniline with a compound selected from the group consisting of (a) a bishalogenomethyl derivative represented by the formula (III):

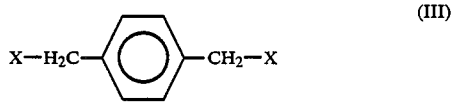

(III)

wherein X represents a halogen atom and (b) an aralkyl alcohol derivative represented by the formula (IV):

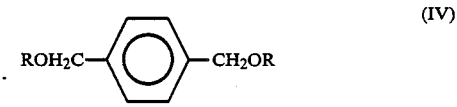

(IV)

wherein R is selected from the group consisting of a hydrogen atom, an acyl group and a lower alkyl group having no more than 4 carbon atoms.

14. The process of claim 13 wherein aniline is present in a molar ratio of from about 1 to about 15 moles of aniline per mole of the compound selected from the group consisting of a bishalogenomethyl derivative and an aralkyl alcohol derivative, said catalyst is an acid catalyst and said reaction is carried out at a temperature of from about 170° to about 240° C.

15. The polymaleimide prepared by the process of claim 4.

16. The polymaleimide prepared by the process of claim 14 wherein the weight average molecular weight is from about 400 to about 15,000.

17. The polymaleimide prepared by the process of claim 14, wherein the melting point is from about 50° C. to about 200° C.

* * * * *